US00PP32544P3

(12) United States Plant Patent
van Zoest

(10) Patent No.: US PP32,544 P3
(45) Date of Patent: Dec. 1, 2020

(54) *CLEMATIS* PLANT NAMED 'ZO09122'

(50) Latin Name: ***Clematis* hybrid**
Varietal Denomination: Zo09122

(71) Applicant: J. van Zoest Beheer B.V., Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 16/602,141

(22) Filed: Aug. 13, 2019

(65) Prior Publication Data

US 2020/0344929 P1 Oct. 29, 2020

(30) Foreign Application Priority Data

Mar. 18, 2019 (QZ) ..... PBR 2019/0724

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./226, 228
See application file for complete search history.

(56) References Cited

PUBLICATIONS

Horticulture Connected, Novelties at Plantarium 2018—Part 3. https://horticultureconnected.ie/news/ornamentals/novelties-at-plantarium-2018-part-3/. 4 pages (Year: 2018).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Clematis* plant named 'Zo09122' that is characterized by its flowers in a range of different color tones throughout the flowering season, its climbing habit, different flower types (single to semi-double) throughout the flowering season, flowers that are facing upright, and its cold hardiness at least to U.S.D.A. Zone 6.

2 Drawing Sheets

Botanical classification: *Clematis* hybrid.
Variety denomination: 'Zo09122'.

CROSS REFERENCE TO A RELATED APPLICATION

This application claims priority to European Community Plant Variety Office (CPVO) Plant Breeder's Rights Application No. 2019/0724 filed on Mar. 18, 2019, the entire contents of which is incorporated by reference herein.

BACKGROUND OF THE INVENTION

The present invention relates to a new and distinct cultivar of *Clematis* of hybrid origin and will be referred to hereafter by its cultivar name 'Zo09122'. 'Zo09122' is a herbaceous perennial grown for use as an landscape plant.

The new Invention arose from an ongoing controlled breeding program in Boskoop, The Netherlands. The objective of the breeding program is to develop hybrid cultivars of *Clematis* with unique and superior garden attributes. In particular, to develop cultivars that are free flowering on young shoots.

The Inventor made a cross in 2006 between an unnamed proprietary plant in the Inventor's breeding program, reference no. 19960159, as the female parent and reference no. 20060200 as the male parent. The Inventor selected 'Zo09122' in 2009, as a single unique plant amongst the seedlings that resulted from the above cross.

Asexual propagation of the new cultivar was first accomplished by softwood stem cuttings under the direction of the Inventor in Boskoop, The Netherlands in 2009. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo09122' as a unique cultivar of *Clematis*.

1. 'Zo09122' exhibits flowers in a range of different color tones throughout the flowering season.
2. 'Zo09122' exhibits a climbing habit.
3. 'Zo09122' exhibits different flower shapes (single to semi-double) throughout the flowering season.
4. 'Zo09122' exhibits flowers that are facing upright.
5. 'Zo09122' exhibits cold hardiness at least to U.S.D.A. Zone 6.

The female parent of 'Zo09122' differs from 'Zo09122' in having flowers that are white in color, single flowers and borne solitary on the peduncle. The male parent of 'Zo09122' differs from 'Zo09122' in having flowers with a range in violet colors with red-purple in the centers towards the base, fully double flowers in the spring, single flowers with 6 to 8 tepals in the summer and susceptibility to wilt (*Phoma clematidina*). 'Zo09122' can be most closely compared to the *Clematis* cultivars 'Venosa Violacea' (not patented) and 'Zo09088' (not patented). Both are similar to 'Zo09122' in having a free flowering habit on young shoots and upward facing flowers. 'Venosa Violacea' differs from 'Zo09122' in having filaments that are green-white in color (lacks a violet color below anther), flower buds that are dark violet in color, and single flowers only. 'Zo09088' differs from 'Zo09122' in having tepal colors that are dark violet to white with prominent dark violet veins, flower buds that are dark violet-purple in color and single flowers only.

STATEMENT DESIGNATING A GRACE PERIOD UNDER 102(B)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventor; including but not limited to disclosures on websites by J Van Zoest, HRS Gardening, Crocus Plants, Taylors Clematis, Floyds Climbers, Nijssen Tuin and Blubs. Plantarium, and *Clematis* on the Web.

BRIEF DESCRIPTION OF THE DRAWINGS

The accompanying colored photographs illustrate the overall appearance and distinct characteristics of the new *Clematis*. The photographs were taken of a three-year-old plant as grown outdoors in a 20-liter pot in Boskoop, The Netherlands.

The photograph in FIG. 1 provides a view of a row of 'Zo09122' in bloom.

Figure 1:
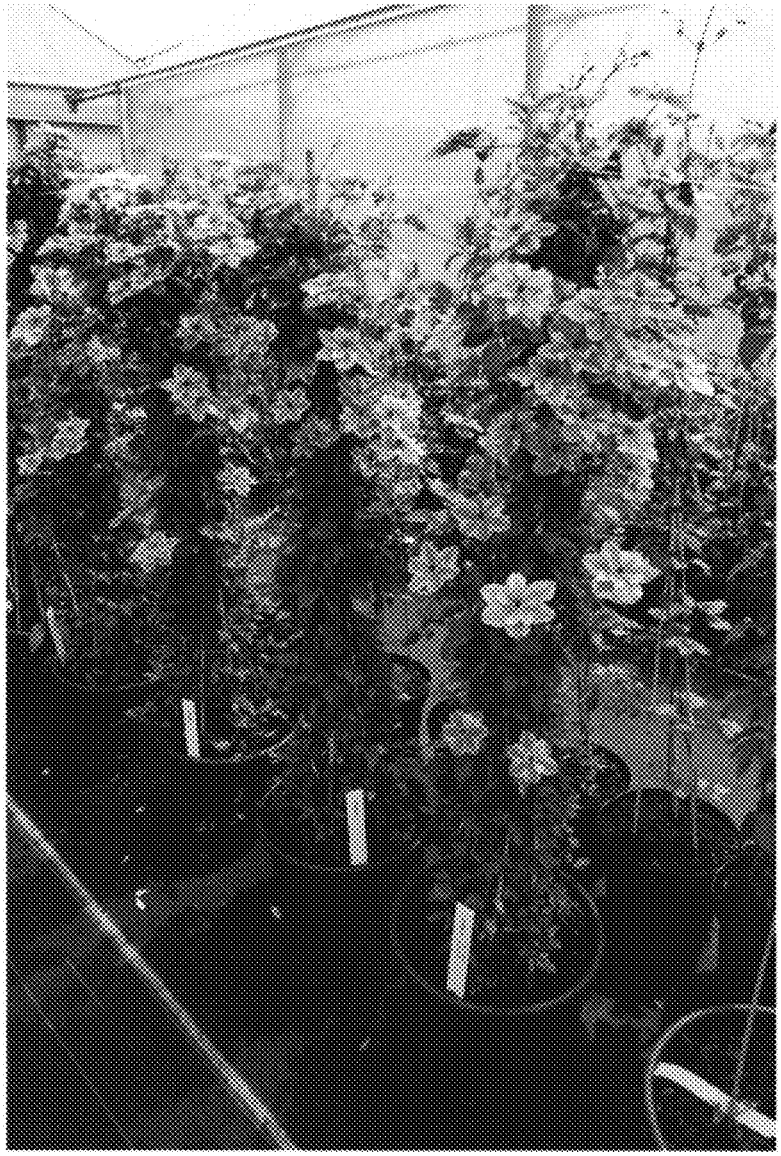
Figure 2:
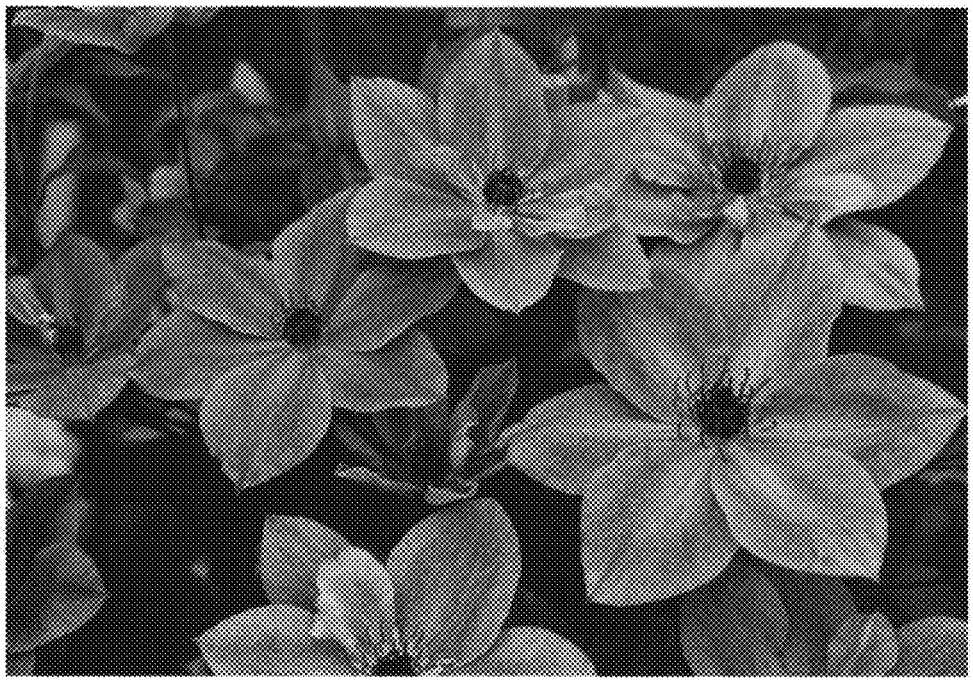

The photograph in FIG. 2 provides a close-up view of single flowers of 'Zo09122' with different tints of violet.

Figure 3:
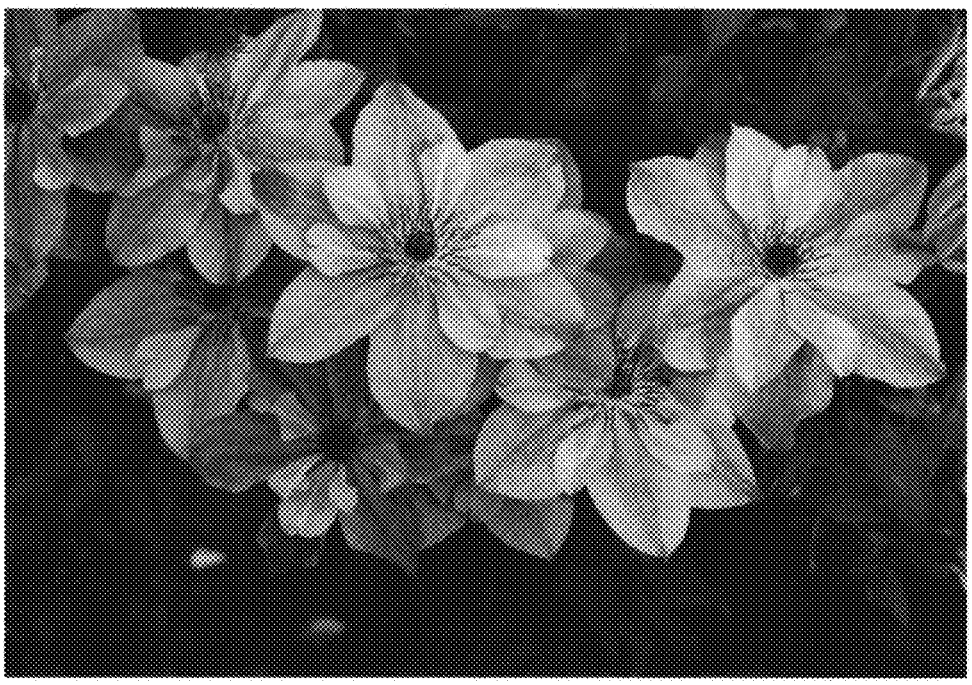

The photograph in FIG. 3 provides a close-up view of FIG. 3 provides a close-up view of semi-double flowers of 'Zo09122' with different tints of violet.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of three-year-old plants as grown outdoors in 2-liter rose containers in Boskoop, The Netherlands. The phenotype of the new cultivar may vary with variations in environmental, climatic and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

- *Blooming period.*—Very freely flowering from June into September in The Netherlands.
- *Plant type.*—Deciduous woody perennial, blooms on new shoots only, only lower part of stems survive winter.
- *Plant habit.*—Climbing.
- *Height and spread.*—A three-year-old plant reaches an average of 3 m in height and 60 cm in width.
- *Cold hardiness.*—At least to U.S.D.A. Zone 6.
- *Diseases and pests.*—No disease or pest problems have been observed, however no susceptibility or resistance to specific causative agents have been identified.
- *Root description.*—Fleshy, N167C in color with tips 155D.
- *Propagation.*—Softwood stem cuttings.
- *Time required for root initiation.*—Roots develop in 5 weeks in summer under greenhouse conditions.
- *Time required for root development.*—75 to 90 days to fully develop in a 7-cm container from a 5 cm cutting.
- *Growth rate.*—Moderate.

Stem description:

- *Shape.*—Round with 6 ribbed angles.
- *Stem color.*—Young upper side; N77A, young lower side; 143C, mature; 183A.
- *Stem size.*—Up to 3 m in length, 0.3 mm in diameter.
- *Stem surface.*—Young; pubescent with short hairs, mature; sparsely pubescent with short hairs.
- *Internode length.*—Up to 15 cm.
- *Strength.*—Very strong and flexible.
- *Branching.*—From the base.

Foliage description:

- *Leaf arrangement.*—Opposite.
- *Division.*—Leaf; ternate to pinnate, leaflet; simple.
- *Leaf size.*—Up to 17 cm in length and 14 cm in width.
- *Leaf attachment.*—Petiolate.
- *Leaf fragrance.*—Sharp (unpleasant).
- *Leaflet shape.*—Broadly ovate to deltoid.
- *Leaflet size.*—Terminal; up to 7 cm in length, up to 4 cm in width, side leaflets; up to 6 cm in length and 3.5 cm in width.
- *Leaflet base.*—Side leaflets; obtuse to sub-cordate, terminal leaflets; obtuse to cordate when cleft.
- *Leaflet apex.*—Acute.
- *Leaflet venation.*—Slightly netted veins with deeper veins, upper surface 146D in color and pubescent, lower surface 138A in color and pubescent and slightly glossy.
- *Leaflet quantity.*—3 to 5.
- *Leaflet margin.*—Entire to sometimes lobed or cleft.
- *Leaflet surface.*—Upper surface; sparsely hairy, veins densely covered with short hairs, lower surface; sparsely hairy and slightly glossy.
- *Leaf color.*—Young upper surface; 146A, young lower surface; 146C, mature upper surface; NN137B, mature lower surface; 148C.
- *Petioles.*—Up to 8 cm in length, 1 mm in diameter, N77A in color, round and slightly canaliculate in shape, aspect is straight to outwards and strongly curling, surface pubescent.
- *Petiolules.*—Rounded in shape, N77A in color, round but slightly canaliculate, sometimes slightly articulate below the leaflet, terminal leaflet; up to 4 cm in length, side leaflets; up to 1.5 mm in length, both 8 mm in diameter, surface sparsely pubescent.

Inflorescence description:

- *Inflorescence type.*—3-flowered dichasial cyme, occasionally solitary.
- *Inflorescence arrangement.*—Terminal and axillary on young shoots, flowering from bottom to top.
- *Inflorescence size.*—Average of 25 cm in length, 20 cm in width and 5 cm in depth when a 3-flowered dichasial cyme.

*Peduncles*.—Up to 10 cm in length and an average of 1.2 mm in width, N77A in color on upper surface and 144A in color on lower surface, round to very slightly ribbed in shape, surface sparsely pubescent, strong.

*Pedicels*.—Up to 15 cm in length, 1.2 mm in diameter, N77A, lower side 144A in color, in color, round in shape, surface is sparsely hairy, more dense close to the flower, strong.

*Flower buds*.—Upright to a bit outward, lanceolate in shape, acuminate apex, obtuse base, up to 4 cm in length and 1.7 cm in diameter, 144B, tinged 144C, surface sparsely pubescent with villous seams.

*Flower fragrance*.—None.

*Lastingness of the flowers*.—Individual flowers last 2 to 3 weeks.

*Flower quantity*.—Average of 20 to 50 flowers per plant.

*Flower type*.—Spreading.

*Flower aspect*.—Upright.

*Flower shape*.—Round and slightly star-shaped, spreading.

*Flower size*.—Up to 10 cm in diameter and 2 cm in depth.

*Flower sex*.—Bisexual.

*Receptacle*.—144C in color and 4 mm in diameter.

*Bracts*.—Simple, sometimes lobed or cleft, lanceolate in shape, up to 6 cm in length and 3 cm in width, acute apex, margins are entire and sometimes lobed or cleft, oblique to obtuse base, both surfaces sparsely pubescent and slightly glossy, color; upper surface 146A, veins 146D, lower surface 146B, veins 138A.

*Tepal number*.—Average of 6 also (pistilloides are present for semi-double and double flowers.

*Tepal shape*.—Elliptic.

*Tepal aspect*.—Spreading.

*Tepal apex*.—Cuspidate.

*Tepal base*.—Cuneate and overlapping.

*Tepal margin*.—Entire.

*Tepal surface*.—Upper surface; glabrous, lower surface; middle section has a few sparse hairs, margin is villous in the middle section.

*Tepal color*.—Upper surface when opening and fully open; base 145D, main tepal color differs in time of year and can have colors in a combination of 83B, N82D, 71B, 76A and NN78B, lower surface when opening and fully open; 144D flushed with 83B, middle section 149D, margins 86C and 86A.

*Tepal size*.—Up to 5 cm in length and an average of 3.5 cm in width.

*Pistilloides*.—Tepal-like pistilloides usually present, irregular to regular in rows, ranges between 1 to 75, when many are present the outer rows are similar to tepals shape, when only a few are present they are usually elliptic to spathulate to irregular in shape, spreading, up to 4 cm in length and 2 cm in width, cuspidate apex, margins entire to flat to irregularly wavy, cuneate base, upper surface color matches tepal color, lower surface color striped 145D and 155D, margins are 86A, upper surface is glabrous, lower surface center is glabrous with margins slightly villous in the middle portion.

*Petaloid staminodes*.—None observed.

Reproductive organs:

*Gynoecium*.—Covered by outer stamens forming a pistil-like urn shape, average of 80 pistils, up to 8 mm in length, ovary; 144B in color and covered with silvery pubescent hairs 202C in color, style; 144D in color, surface is silvery plumose 202C in color, stigma; slightly bent outwards and slightly club-shaped, N79A in color, glabrous surface.

*Androecium*.—75 to 125, filaments; up to 7 mm in length, 1 mm in width and linear in shape, surface is glabrous and pubescent below the anther, color; outer filaments NN155D, inner filaments 150D, anthers; 5 mm in length, 0.5 mm in width, linear in shape, and N186C in color, glabrous surface, pollen; 4D in color and abundant in quantity, connective; straight in aspect, N77C in color, glabrous and sometimes pubescent at the base.

*Seed*.—Seed head; up to 4.5 cm in diameter, globular in shape, 50% of the pistils might set seed by open pollination, seed; average of 40, 6 mm in length, 5 mm in width, 146C in color, sparsely pubescent, seed style; up to 2 cm in length, 144C in color, surface is sparsely pubescent with silver hairs, seed stigma; strongly bent and 178A in color.

It is claimed:

1. A new and distinct cultivar of *Clematis* plant named 'Zo09122' as herein illustrated and described.

* * * * *